United States Patent
Amancha et al.

(10) Patent No.: US 9,839,611 B2
(45) Date of Patent: *Dec. 12, 2017

(54) SUBLINGUAL BUPRENORPHINE SPRAY

(71) Applicant: Insys Development Company, Inc., Chandler, AZ (US)

(72) Inventors: Kiran P. Amancha, Chandler, AZ (US); Chandeshwari S. Chilampalli, Phoenix, AZ (US); Venkat R. Goskonda, Phoenix, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,630

(22) Filed: Oct. 27, 2015

(65) Prior Publication Data

US 2016/0045430 A1  Feb. 18, 2016

Related U.S. Application Data

(63) Continuation-in-part of application No. 14/469,063, filed on Aug. 26, 2014, now Pat. No. 9,216,175.

(60) Provisional application No. 61/875,837, filed on Sep. 10, 2013.

(51) Int. Cl.
| | |
|---|---|
| *A61K 47/10* | (2017.01) |
| *A61K 9/00* | (2006.01) |
| *A61K 31/4748* | (2006.01) |
| *A61K 31/485* | (2006.01) |

(52) U.S. Cl.
CPC .......... *A61K 9/006* (2013.01); *A61K 31/4748* (2013.01); *A61K 31/485* (2013.01); *A61K 47/10* (2013.01)

(58) Field of Classification Search
CPC ....... A61K 31/485; A61K 47/10; A61K 9/006
See application file for complete search history.

(56) References Cited

U.S. PATENT DOCUMENTS

| | | |
|---|---|---|
| 6,365,596 B1 | 4/2002 | Valenti |
| 6,413,496 B1 | 7/2002 | Goodman et al. |
| 7,501,113 B2 | 3/2009 | Blondino et al. |
| 7,666,876 B2 | 2/2010 | Birch et al. |
| 8,211,946 B2 | 7/2012 | Whittle |
| 8,475,832 B2 | 7/2013 | Myers et al. |
| 2003/0003113 A1 | 1/2003 | Lewandowski |
| 2003/0166624 A1 | 9/2003 | Gale et al. |
| 2003/0190290 A1 | 10/2003 | Ross |
| 2004/0192714 A1 | 9/2004 | Boer et al. |
| 2007/0148097 A1 | 6/2007 | Finn et al. |
| 2009/0117054 A1 | 5/2009 | Crooks et al. |
| 2009/0176834 A1 | 7/2009 | Kottayil et al. |
| 2009/0270438 A1 | 10/2009 | Booles et al. |
| 2010/0015183 A1 | 1/2010 | Finn et al. |
| 2010/0087470 A1 | 4/2010 | Oksche et al. |
| 2010/0120812 A1 | 5/2010 | Chapleo et al. |
| 2010/0233257 A1 | 9/2010 | Herry et al. |
| 2011/0189259 A1 | 8/2011 | Vasisht et al. |
| 2011/0245288 A1 | 10/2011 | Stinchcomb et al. |
| 2011/0280916 A1 | 11/2011 | Blondino et al. |
| 2013/0109747 A1 | 5/2013 | Whittle |

FOREIGN PATENT DOCUMENTS

| | | | |
|---|---|---|---|
| GB | 2461681 A | 1/2010 | |
| WO | WO 98/43673 | * 3/1998 | ............. A61K 47/10 |
| WO | 2007087431 A2 | 8/2007 | |
| WO | 2009120889 | 10/2009 | |

OTHER PUBLICATIONS

Dumitriu (Polymeric Biomaterials, Revised and Expanded 2001, CRC Press; p. 8).*
Kuhlman et al. (J. Anal. Toxicol 1996; 20:369-378).*
Lado et al. (Z. Naturforsch. 2004;59c:354-358).*
International Search Report and the Written Opinion for corresponding application PCT/US14/52699 dated Nov. 26, 2014.
Panchagnula R. et al., Transdermal delivery of naloxone: effect of water, propylene glycol, ethanol and their binary combinations on permeation through rat skin, Int J Pharm, May 21, 2001, 219(1-2), 95-105.
Prausnitz M.R., et al., Transdermal drug delivery, Nat Biotechnol, Nov. 2008, 26(11), 1261-1268.

* cited by examiner

*Primary Examiner* — Ernst V Arnold
(74) *Attorney, Agent, or Firm* — Wood, Phillips, Katz, Clark & Mortimer

(57) ABSTRACT

The invention provides sublingual formulations containing buprenorphine, a pharmaceutically acceptable salt thereof, or a derivative thereof. The invention further provides sublingual formulations containing buprenorphine and naloxone, pharmaceutically acceptable salts thereof or derivatives thereof. The invention further provides a method of treating pain or opioid dependence by administering sublingual formulations containing buprenorphine, a pharmaceutically acceptable salt thereof, or a derivative thereof to a patient in need thereof.

18 Claims, No Drawings

SUBLINGUAL BUPRENORPHINE SPRAY

FIELD OF THE INVENTION

The invention is directed to sublingual spray formulations containing buprenorphine, a pharmaceutically acceptable salt thereof, or a derivative thereof. The invention is further directed to sublingual spray formulations containing buprenorphine and naloxone, pharmaceutically acceptable salts thereof or derivatives thereof. The invention is further directed to a method of treating pain or opioid dependence by administering sublingual spray formulations containing buprenorphine or buprenorphine and naloxone, pharmaceutically acceptable salts thereof, or derivatives thereof to a patient in need thereof.

BACKGROUND OF THE INVENTION

Buprenorphine is a semi-synthetic opioid and a partial μ-opioid receptor agonist and has the following structure:

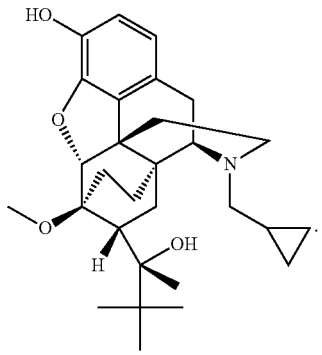 [SMILES: CO[C@@]12CC[C@@]3(C[C@@H]1[C@](C)(O)C(C)(C)C)[C@H]1Cc4ccc(O)c5c4[C@@]3(CCN1CC1CC1)[C@H]2O5]

Activation of the μ-opioid receptor leads to antinociception and is the pathway by which opioids such as morphine and fentanyl reduce acute and chronic pain. Buprenorphine has advantages over other opioids such as morphine and fentanyl in that it is only a partial instead of a full agonist of the opioid receptor-like receptor 1 ("ORL1"). Activation of ORL1 has been reported to weaken the analgesic effect induced by the activation of the μ-opioid receptor. Additionally, buprenorphine is an antagonist of δ- and κ-opioid receptors, whose activation has anti-analgesic and psychotomimetic effects, respectively. Buprenorphine is also useful in the management of opioid dependence. The slow binding of buprenorphine to the μ-opioid receptor along with its strong affinity allows for pain management at relatively low blood concentrations and the slow disassociation of buprenorphine from the μ-opioid receptor results in a lack of withdrawal symptoms.

Buprenorphine is currently available in transdermal patches, intravenous injection, tablet and film strip formulations. Commercially available buprenorphine formulations include Butrans® (Butrans is a registered trademark of Purdue Pharma L.P.), a 7 day transdermal patch that releases buprenorphine at 5, 10 or 20 mcg/hr, and Temgesic, a 0.2 mg sublingual tablet, are used for the treatment of chronic pain. Buprenex® (Buprenex is a registered trademark of Reckitt Benckiser Healthcare (UK) Limited) is a 0.3 mg/mL injectable solution used for the treatment of acute pain. Subutex® (Subutex is a registered trademark of Reckitt Benckiser Healthcare (UK) Limited) and Suboxone® (Suboxone is a registered trademark of Reckitt Benckiser Healthcare (UK) Limited) are tablets used in the treatment of opioid dependence. Subutex® is available in 2 mg and 8 mg sublingual doses of buprenorphine. Suboxone® contains both buprenorphine and naloxone in a 4:1 ratio. Suboxone® is available in tablet form in 2 mg and 8 mg doses. Suboxone® is also available in a sublingual film strip formulation that dissolves faster and is not lost by accidental swallowing.

Naloxone has the following structure and is synthesized from thebaine:

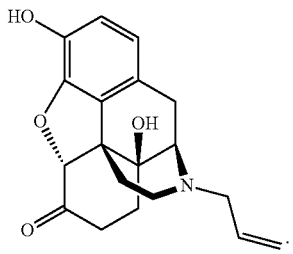

Naloxone is most commonly used to treat patients suffering from opioid dependence or overdose because it is a competitive μ-opioid antagonist that blocks the effects of opioids.

While there are various formulations currently available, there exists a need in the art for a sublingual spray formulation containing buprenorphine or buprenorphine and naloxone, pharmaceutically acceptable salts thereof, or derivatives thereof. Such a formulation should be safe, be easy to administer, have a high bioavailability, and be storage stable.

SUMMARY OF THE INVENTION

In certain embodiments, the present invention is directed to a sublingual spray formulation comprising an effective amount of buprenorphine, a pharmaceutically acceptable salt thereof, or a derivative thereof, water as a solvent, and a mixture of an alcohol and a glycol as a cosolvent.

In certain embodiments, the present invention is directed to a sublingual spray formulation comprising:
 an effective amount of buprenorphine, a pharmaceutically acceptable salt thereof, or a derivative thereof;
 naloxone, a pharmaceutically acceptable salt thereof, or a derivative thereof; water as a solvent; and
 a mixture of an alcohol and a glycol as a cosolvent.

In certain embodiments, the present invention is directed to a sublingual spray formulation comprising an effective amount of buprenorphine, a pharmaceutically acceptable salt thereof, or a derivative thereof wherein the formulation has a pH from about 3.5 to about 5.5.

In certain embodiments, the present invention is directed to a sublingual spray formulation comprising:
 an effective amount of buprenorphine, a pharmaceutically acceptable salt thereof, or a derivative thereof;
 water as a solvent;
 a mixture of an alcohol and a glycol as a cosolvent; and
 an antioxidant.

In certain embodiments, the present invention is directed to a sublingual spray formulation comprising:
 an effective amount of buprenorphine, a pharmaceutically acceptable salt thereof, or a derivative thereof;
 water as a solvent;
 a cosolvent selected from the group consisting of an alcohol and a glycol or a mixture thereof; and
 an antioxidant In certain embodiments, the present invention is directed to a sublingual spray formulation comprising:
- an effective amount of buprenorphine, a pharmaceutically acceptable salt thereof, or a derivative thereof;
- water as a solvent;
- a cosolvent selected from the group consisting of an alcohol and a glycol or a mixture thereof; and
- an antioxidant.

In certain embodiments, the present invention is directed to a sublingual spray formulation comprising:
- an effective amount of buprenorphine, a pharmaceutically acceptable salt thereof, or a derivative thereof;
- water as a solvent;
- a mixture of an alcohol and a glycol as a cosolvent; and
- an antioxidant selected from the group consisting of butylated hydroxyanisole ("BHA"), butylated hydroxytoluene ("BHT"), methionine, sodium ascorbate, sodium thiosulfate, thioglycerol, cysteine hydrochloride monohydrate and a mixture thereof.

In certain embodiments, the present invention is directed to a sublingual spray formulation comprising:
- an effective amount of buprenorphine, a pharmaceutically acceptable salt thereof, or a derivative thereof;
- water as a solvent;
- a mixture of ethanol and propylene glycol as a cosolvent; and
- an antioxidant selected from the group consisting of BHA, BHT, methionine, sodium ascorbate, sodium thiosulfate and thioglycerol, cysteine hydrochloride monohydrate or a mixture thereof.

In certain embodiments, the present invention is directed to a sublingual spray formulation comprising:
- an effective amount of buprenorphine, a pharmaceutically acceptable salt thereof, or a derivative thereof;
- water as a cosolvent;
- a cosolvent selected from the group consisting of ethanol, propylene glycol, and a mixture thereof;
- an antioxidant selected from the group consisting of BHA, BHT, methionine, sodium ascorbate, sodium thiosulfate, thioglycerol, cysteine hydrochloride monohydrate and a mixture thereof; and
- a permeation enhancer.

In certain embodiments, the present invention is directed to a sublingual spray formulation comprising:
- an effective amount of buprenorphine, a pharmaceutically acceptable salt thereof, or a derivative thereof;
- water as a solvent;
- a cosolvent selected from the group consisting of ethanol, propylene glycol, and a mixture thereof;
- an antioxidant selected from the group consisting of BHA, BHT, methionine, sodium ascorbate, sodium thiosulfate, thioglycerol, cysteine hydrochloride monohydrate and a mixture thereof; and
- menthol as a permeation enhancer.

In certain embodiments, the present invention is directed to a sublingual spray formulation comprising:
- an effective amount of buprenorphine, a pharmaceutically acceptable salt thereof, or a derivative thereof;
- water as a solvent;
- a cosolvent selected from the group consisting of ethanol, propylene glycol, and a mixture thereof;
- an antioxidant selected from the group consisting of BHA, BHT, methionine, sodium ascorbate, sodium thiosulfate, thioglycerol, cysteine hydrochloride monohydrate and a mixture thereof; and
- a pH adjustor.

In certain embodiments, the present invention is directed to a sublingual spray formulation comprising:
- an effective amount of buprenorphine, a pharmaceutically acceptable salt thereof, or a derivative thereof;
- water as a solvent;
- a cosolvent selected from the group consisting of ethanol, propylene glycol, and a mixture thereof;
- an antioxidant selected from the group consisting of BHA, BHT, methionine, sodium ascorbate, sodium thiosulfate, thioglycerol, cysteine hydrochloride monohydrate and a mixture thereof; and
- citric acid as a pH adjustor selected from the group consisting of citric acid, sodium hydroxide and a mixture thereof.

In certain embodiments, the present invention is directed to a sublingual spray formulation comprising:
- an effective amount of buprenorphine, a pharmaceutically acceptable salt thereof, or a derivative thereof;
- water as a solvent;
- a solubilizer selected from the group consisting of cyclodextrins such as hydroxypropyl beta-cyclodextrin ("HPβCD"), sulfobutylether cyclodextrin, and a mixture thereof; and
- an antioxidant selected from the group consisting of BHA, BHT, methionine, sodium ascorbate, sodium thiosulfate, thioglycerol, cysteine hydrochloride monohydrate and a mixture thereof.

In preferred embodiments, the present invention is directed to a sublingual spray formulation comprising:
- an amount of buprenorphine from about 0.05% to about 10% w/w;
- an amount of water from about 10% to about 95% w/w;
- an amount of cosolvent from about 5% to about 90% w/w; and
- an amount of antioxidant from about 0.0001% to about 0.5% w/w; and
- optionally, menthol as a permeation enhancer.

In a more preferred embodiment, the present invention is directed to a sublingual spray formulation comprising:
- an amount of buprenorphine from about 0.08% to about 1.3% w/w;
- an amount of water from about 38% to about 40% w/w;
- a cosolvent consisting of a mixture of ethanol in an amount of 55% w/w and propylene glycol in an amount of about 5% w/w;
- an antioxidant consisting of a mixture of butylated hydroxyanisole (BHA) in an amount of about 0.01% w/w and butylated hydroxytoluene (BHT) in an amount of about 0.005% w/w; and
- menthol in an amount of about 0.05% w/w.

In preferred embodiments, the present invention is directed to a sublingual spray formulation comprising:
- buprenorphine, a pharmaceutically acceptable salt thereof or a derivative thereof at an amount from about 0.05% to about 10% w/w;
- naloxone, a pharmaceutically acceptable salt thereof or a derivative thereof at an amount from about 0.005% to about 3% w/w;
- water as a solvent in an amount from about 10% w/w to about 95% w/w;
- a cosolvent consisting of a mixture of an alcohol and a glycol in an amount from about 5% to about 90% w/w;
- an antioxidant in an amount from about 0.001% to about 0.2% w/w; and
- a chelating agent in an amount from about 0.001% to about 0.1% w/w.

In preferred embodiments, the present invention is directed to a sublingual spray formulation comprising:
buprenorphine, a pharmaceutically acceptable salt thereof or a derivative thereof at an amount from about 0.05% to about 10% w/w;
naloxone, a pharmaceutically acceptable salt thereof or a derivative thereof at an amount from about 0.005% to about 3% w/w;
water as a solvent in an amount from about 10% w/w to about 95% w/w;
a cosolvent consisting of a mixture of an alcohol and a glycol in an amount from about 5% to about 90% w/w;
an antioxidant in an amount from about 0.001% to about 0.2% w/w;
a chelating agent in an amount from about 0.001% to about 0.1% w/w; and
menthol as a permeation enhancer.

In certain preferred embodiments the present invention is directed to a sublingual spray formulation comprising:
buprenorphine, a pharmaceutically acceptable salt thereof or a derivative thereof at an amount from about 1.4% to about 8.6% w/w;
naloxone, a pharmaceutically acceptable salt thereof or a derivative thereof at an amount from about 0.4% to about 2.4% w/w;
water as a solvent in an amount from about 28% w/w to 38% w/w;
a cosolvent consisting of a mixture of ethanol in an amount from about 55% w/w and propylene glycol in an amount of about 5% w/w;
an antioxidant selected from a group consisting of butylated hydroxyanisole, butylated hydroxytoluene, methionine, sodium ascorbate, sodium thiosulfate, thioglycerol, cysteine Hydrochloride monohydrate, and a mixture thereof in an amount from about 0.001% to about 0.2% w/w, preferably sodium ascorbate in an amount of about 0.02% w/w;
disodium edetate in an amount of about 0.005% w/w; and
menthol in an amount of about 0.05% w/w.

In certain preferred embodiments the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.4% to about 2.7% w/w;
water as a solvent in an amount from about 27.4% w/w to 39.7% w/w;
a cosolvent consisting of a mixture of ethanol in an amount from about 55% w/w and propylene glycol in an amount from about 5% w/w; and
an antioxidant selected from a group consisting of butylated hydroxyanisole, butylated hydroxytoluene, methionine, sodium ascorbate, sodium thiosulfate, thioglycerol, cysteine Hydrochloride monohydrate and a mixture thereof in an amount from about 0.001% to about 0.2% w/w.

In certain preferred embodiments the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.005% to about 2.7% w/w;
water as a solvent in an amount from about 27.4% w/w to 39.7% w/w;
a cosolvent consisting of a mixture of ethanol in an amount of about 55% w/w and propylene glycol in an amount of about 5% w/w; and
an antioxidant selected from a group consisting of butylated hydroxyanisole, butylated hydroxytoluene, methionine, sodium ascorbate, sodium thiosulfate, thioglycerol, cysteine Hydrochloride monohydrate, and a mixture thereof in an amount from about 0.001% to about 0.2% w/w.

In certain preferred embodiments the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.005% to about 3% w/w;
water as a solvent in an amount from about 27.4% w/w to 39.7% w/w; a cosolvent consisting of a mixture of ethanol in an amount of about 55% w/w and propylene glycol in an amount of about 5% w/w;
an antioxidant selected from a group consisting of butylated hydroxyanisole, butylated hydroxytoluene, methionine, sodium ascorbate, sodium thiosulfate, thioglycerol, cysteine Hydrochloride monohydrate, and a mixture thereof; and
ethylenediaminetetraacetic acid disodium (disodium edetate) as a chelating agent in an amount of about 0.005% w/w or citric acid as a pH adjustor in an amount from about 0.0025 to 10% w/w.

In certain embodiments, the sublingual spray formulations of the present invention contain naloxone in an amount that discourages improper administration of the formulations. When the naloxone containing formulations are properly administered, the naloxone is delivered at a rate that is below that which would be therapeutic. In this context, "therapeutic" refers to an amount of naloxone that would block the effects of the buprenorphine that is concurrently administered in the sublingual spray formulation. If the formulations are improperly used, however, the naloxone in the formulation could be sufficient to block the effects of buprenorphine.

In certain embodiments, the present invention is directed to methods for treating pain comprising administering a sublingual spray formulation of the present invention to a patient.

In certain embodiments, the present invention is directed to methods for treating opioid dependence comprising administering a sublingual spray formulation of the present invention to a patient.

In an embodiment, the present invention is directed to sublingual spray formulations wherein the $C_{max}$ (ng/mL) of buprenorphine is from about 0.6 to about 0.8. In a preferred embodiment, the $C_{max}$ (ng/mL) of buprenorphine is 0.76 following sublingual administration.

In yet another embodiment, the present invention is directed to sublingual spray formulations wherein the $T_{max}$ of buprenorphine is from about 1.5 to about 1.9 hours. In a preferred embodiment, the $T_{max}$ of buprenorphine is about 1.75 hours following sublingual administration.

In yet another embodiment, the present invention is directed to sublingual spray formulations wherein the $C_{max}$ (ng/mL) of buprenorphine is from about 1.2 to about 1.5. In a preferred embodiment, the $C_{max}$ (ng/mL) of buprenorphine is about 1.38 following sublingual administration.

In a further embodiment, the present invention is directed to sublingual spray formulations wherein the $T_{max}$ of buprenorphine is from about 1.2 to about 1.7 hours. In a preferred embodiment, the $T_{max}$ of buprenorphine is about 1.5 hours following sublingual administration.

In another embodiment, the present invention is directed to sublingual spray formulations wherein greater than 98% of the formulation particles are greater than 10 microns in diameter during administration.

In another embodiment, the present invention is directed to sublingual spray formulations wherein the mean Dv(10) is from about 10 to about 30 microns during administration.

In another embodiment, the present invention is directed to sublingual spray formulations wherein the mean Dv(50) is from about 30 to about 80 microns during administration.

In another embodiment, the present invention is directed to sublingual spray formulations wherein the mean Dv(90) is from about 80 to about 200 microns during administration.

In a further embodiment, the present invention is directed to sublingual spray formulations that when administered provide a spray plume ovality ratio of from about 1.1 to 2.4.

In yet another embodiment, the invention is directed to sublingual formulations that when administered provide a plume width of from about 25 to about 45 millimeters.

In a further embodiment, the invention is directed to sublingual formulations that when administered provide a plume angle of from about 30 to about 55 degrees.

In yet another embodiment, the invention is directed to sublingual formulations that when administered provide a D(4,3) of 55 to 95 microns.

In an additional embodiment, the invention is directed to sublingual formulations that when administered provide a spray span ((Dv90-Dv10)/Dv50) of from about 1.2 to about 3.3.

DETAILED DESCRIPTION OF THE INVENTION

The present invention is directed to a sublingual spray formulation comprising an effective amount of buprenorphine or buprenorphine and naloxone, pharmaceutically acceptable salts thereof, or derivatives thereof. The present invention further relates to a method of treating pain or opioid dependence by administering an effective amount of a sublingual spray formulation of the present invention to a patient in need thereof.

The present invention is further directed to a sublingual spray formulation comprising an effective amount of buprenorphine or buprenorphine and naloxone, pharmaceutically acceptable salts thereof, or derivatives thereof, a solvent, a cosolvent and an antioxidant.

Applicants developed new sublingual buprenorphine and buprenorphine/naloxone formulations that unexpectedly are storage stable, safe and effective. Specifically, Applicants were surprised that the formulations were stable at high temperatures (40 degrees Celsius) for an extended period of time (see Examples 1 and 2 below). Further, Applicants unexpectedly found that the formulations provided a quick onset of action and bioavailability (as demonstrated by pharmacokinetic studies, see Example 3 below). The formulations upon administration exhibit excellent droplet size distribution, as well.

As used herein the term "patient" refers but is not limited to a person that is being treated for pain, opioid dependence or another affliction or disease that can be treated with buprenorphine.

As used herein the term "pharmaceutically acceptable" refers to ingredients that are not biologically or otherwise undesirable in a sublingual dosage form.

As used herein the term "effective amount" refers to the amount necessary to treat a patient in need thereof.

Pharmaceutically acceptable salts that can be used in accordance with the current invention include but are not limited to hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In preferred embodiments the pharmaceutically acceptable salt is hydrochloride.

Derivatives of buprenorphine that can be used in accordance with the current invention include but are not limited norbuprenorphine, thenorphine, demethoxybuprenorphine and esters and diastereomers of buprenorphine.

The solvent used with the present invention is United States Pharmacopeia ("USP") purified water.

Cosolvents that can be used in accordance with the current invention are alcohols, and glycols or a mixture thereof.

Alcohols that can be used in accordance with the current invention include but are not limited to methanol, ethanol, propyl alcohol, and butyl alcohol.

Glycols that can be used in accordance with the current invention include but are not limited to propylene glycol, butylene glycol and polyethylene glycols such as PEG 200 and PEG 400 and the like.

In preferred embodiments the cosolvent is ethanol or propylene glycol or a mixture thereof.

In more preferred embodiments the amount of cosolvent included in the formulation is from about 5% to about 90% w/w.

In other more preferred embodiments the amount of cosolvent included in the formulation is from about 2 to about 10% propylene glycol. In a most preferred embodiment the amount of cosolvent is about 5% w/w propylene glycol.

In other more preferred embodiments the amount of cosolvent included in the formulation is about 40% w/w to about 60% w/w ethanol. In a most preferred embodiment the amount of cosolvent is about 55% w/w ethanol.

In other more preferred embodiments the cosolvent is a mixture of propylene glycol at about 5% w/w and ethanol at about 55% w/w.

Solubilizers that can be used in accordance with the current invention are hydroxpropyl beta-cyclodextrin ("HPβCD") and sulfobutylether cyclodextrin or a mixture thereof.

In preferred embodiments the solubilizer is HPβCD.

In more preferred embodiments the amount of HPβCD is from about 10% w/w to 40% w/w. In a most preferred embodiment the amount of HPβCD is about 30% w/w.

Antioxidants that can be used in accordance with the current invention include but are not limited to butylated hydroxyanisole ("BHA"), butylated hydroxytoluene ("BHT"), methionine, sodium ascorbate, sodium thiosulfate and thioglycerol, cysteine Hydrochloride monohydrate or a mixture thereof.

In preferred embodiments the amount of antioxidant included in the formulation is from about 0.001% to about 0.05% w/w.

In more preferred embodiments the amount of antioxidant is about 0.01% w/w of BHA.

In other more preferred embodiments the antioxidant is a mixture of about 0.01% w/w of BHA and about 0.005% w/w of BHT.

In other more preferred embodiments the antioxidant is about 0.01% w/w of sodium thiosulfate.

In other more preferred embodiments the antioxidant is about 0.02% w/w of sodium ascorbate.

Permeation enhancers that can be used in accordance with the current invention include but are not limited to menthol, Tween® 80 (Tween is a registered trademark of Uniqema Americas, LLC), sodium lauryl sulfate, glyceryl oleate, oleic acid, cetylpyridium chloride, and sodium desoxy cholate.

In preferred embodiments the amount of permeation enhancer is from about 0.001% to about 0.1% w/w.

In more preferred embodiments the amount of permeation enhancer is about 0.05% w/w of menthol.

Chelating agents that can be used in accordance with the present invention include but are not limited to ethylenediaminetetraacetic acid disodium ("disodium edetate" or edetate disodium dihyrdate").

In preferred embodiments the amount of disodium edetate is about 0.005% to about 0.01% w/w.

Formulations of the present invention may have a pH range from about 3.0 to about 7.0, preferably from about 3.5 to about 5.5 and more preferably from about 3.8 to about 5.1. pH adjustors that can be used in accordance with the present invention include but are not limited to citric acid, sodium hydroxide and a mixture thereof. In preferred embodiments the amount of citric acid is from about 2% to about 20% w/w. In more preferred embodiments the amount of citric acid is about 15%. In other more preferred embodiments the amount of citric acid is about 10%.

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

As used herein "% w/w" refers to the percent weight of the total formulation.

Representative Embodiments

In a more preferred embodiment the sublingual spray formulation comprises:
    an amount of buprenorphine of about 0.54% w/w;
    an amount of water of about 39.4% w/w;
    a cosolvent as a mixture of ethanol in an amount of about 55% w/w and propylene glycol in an amount of about 5% w/w;
    an antioxidant as a mixture of BHA in an amount of about 0.01% w/w and BHT in an amount of about 0.005% w/w; and
    menthol as a permeation enhancer in an amount of about 0.05% w/w.

In another more preferred embodiment the sublingual spray formulation comprises:
    an amount of buprenorphine of about 0.54% w/w;
    an amount of water of about 39.4% w/w;
    a cosolvent as a mixture of ethanol in an amount of about 55% w/w and propylene glycol in an amount of about 5% w/w;
    sodium thiosulfate as an antioxidant in an amount of about 0.01% w/w;
    menthol as a permeation enhancer in an amount of about 0.05% w/w; and
    citric acid as a pH adjustor in an amount of about 0.002% w/w.

In another more preferred embodiment the sublingual spray formulation comprises:
    an amount of buprenorphine of about 0.54% w/w;
    an amount of water of about 39.39% w/w;
    a cosolvent as a mixture of ethanol in an amount of about 55% w/w and propylene glycol in an amount of about 5% w/w;
    sodium ascorbate as an antioxidant in an amount of about 0.01% w/w;
    menthol as a permeation enhancer in an amount of about 0.05% w/w; and
    disodium edetate as a chelating agent in an amount of about 0.01% w/w.

In a most preferred embodiment the sublingual spray formulation comprises:
    an amount of buprenorphine of about 0.54% w/w;
    an amount of water of about 39.45% w/w;
    a cosolvent as a mixture of ethanol in an amount of about 55% w/w and propylene glycol in an amount of about 5% w/w; and
    BHA as an antioxidant in an amount of about 0.01% w/w.

In a more preferred embodiment the sublingual spray formulation comprises:
    an amount of buprenorphine of about 8.602% w/w;
    an amount of naloxone of about 2.44% w/w;
    an amount of water of about 29% w/w;
    an amount of sodium thiosulfate of about 0.01% w/w; and
    an amount of citric acid of about 0.0025% w/w.

In a more preferred embodiment the sublingual spray formulation comprises:
    an amount of buprenorphine of about 8.602% w/w;
    an amount of naloxone of about 2.44% w/w;
    an amount of water of about 29% w/w;
    an amount of sodium thiosulfate of about 0.01% w/w; and
    an amount of disodium edetate of about 0.005% w/w.

In a more preferred embodiment the sublingual spray formulation comprises:
    an amount of buprenorphine of about 8.602% w/w;
    an amount of naloxone of about 2.44% w/w;
    an amount of water of about 29% w/w;
    an antioxidant as a mixture of BHA in an amount of about 0.01% w/w and BHT in an amount of about 0.005% w/w; and
    an amount of disodium edetate of about 0.005% w/w.

In a more preferred embodiment the sublingual spray formulation comprises:
    an amount of buprenorphine of about 8.602% w/w;
    an amount of naloxone of about 2.44% w/w;
    an amount of water of about 29% w/w;
    an amount of sodium ascorbate of about 0.02% w/w; and
    an amount of disodium edetate of about 0.005% w/w.

In a more preferred embodiment the sublingual spray formulation comprises:
    an amount of buprenorphine of about 8.39% w/w;
    an amount of naloxone of about 2.37% w/w;
    an amount of water of about 29% w/w;
    an amount of ethanol of about 55% w/w;
    an amount of propylene glycol of about 5% w/w;
    an amount of sodium ascorbate of about 0.02% w/w;
    an amount of disodium edetate of about 0.005% w/w; and
    an amount of menthol of about 0.05% w/w.

In a more preferred embodiment the sublingual spray formulation comprises:
    an amount of buprenorphine of about 5.554% w/w;
    an amount of naloxone of about 1.57% w/w;
    an amount of water of about 33% w/w;
    an amount of ethanol of about 55% w/w;
    an amount of propylene glycol of about 5% w/w;
    an amount of sodium ascorbate of about 0.02% w/w;
    an amount of disodium edetate of about 0.005% w/w; and
    an amount of menthol of about 0.05% w/w.

In a more preferred embodiment the sublingual spray formulation comprises:
  an amount of buprenorphine of about 2.84% w/w;
  an amount of naloxone of about 0.804% w/w;
  an amount of water of about 36% w/w;
  an amount of ethanol of about 55% w/w;
  an amount of propylene glycol of about 5% w/w;
  an amount of sodium ascorbate of about 0.02% w/w;
  an amount of disodium edetate of about 0.005% w/w; and
  an amount of menthol of about 0.05% w/w.

In a more preferred embodiment the sublingual spray formulation comprises:
  an amount of buprenorphine of about 1.42% w/w;
  an amount of naloxone of about 0.402% w/w;
  an amount of water of about 38% w/w;
  an amount of ethanol of about 55% w/w;
  an amount of propylene glycol of about 5% w/w;
  an amount of sodium ascorbate of about 0.02% w/w;
  an amount of disodium edetate of about 0.005% w/w; and
  an amount of menthol of about 0.05% w/w.

In another more preferred embodiment the sublingual spray formulation comprises:
  an amount of buprenorphine from about 0.813% to about 1.3% w/w, preferably 0.0813% w/w, 0.1625% w/w, 0.325% w/w, 0.65% w/w or 1.3% w/w;
  an amount of BHA of about 0.01% w/w;
  an amount of BHT of about 0.005% w/w;
  an amount of ethanol of about 55% w/w;
  an amount of propylene glycol of about 5% w/w; and
  an amount of water from about 39.8537% to about 38.635% w/w, preferably 39.8537% w/w, 39.7725% w/w, 39.61% w/w, 39.285% w/w or 38.635% w/w.

The following examples are intended to illustrate the present invention and to teach one of ordinary skill in the art how to make and use the invention. They are not intended to be limiting in any way.

EXAMPLES

Example 1: Stable Buprenorphine Formulations

Method of Making the Formulations

Sublingual spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Active pharmaceutical ingredient/s was/were added to the final solution and mixed until dissolved.

Formulations

TABLE 1

Stable Sublingual Buprenorphine Spray Formulations

| Formulation | Control | #1 | #2 | #3 | #4 | #5 | #6 | #7 | #8 | #9 |
|---|---|---|---|---|---|---|---|---|---|---|
| Buprenorphine HCl | 0.538 | 0.538 | 0.538 | 0.538 | 0.538 | 0.538 | 0.538 | 0.538 | 0.538 | 0.538 |
| Water (USP) | 39.462 | 39.452 | 39.397 | 39.372 | 89.427 | 94.427 | 39.39 | 39.4 | 39.405 | 69.472 |
| Ethanol | 55 | 55 | 55 | 55 | 10 | | 55 | 55 | 55 | |
| Propylene Glycol | 5 | 5 | 5 | 5 | | 5 | 5 | 5 | 5 | |
| HPβCD | | | | | | | | | | 30 |
| BHA | | 0.01 | 0.01 | | | | | | | |
| BHT | | | 0.005 | | | | | | | |
| Sodium Ascorbate | | | | 0.02 | 0.02 | 0.02 | 0.01 | | | 0.02 |
| Sodium Thiosulfate | | | | | | | | 0.01 | | |
| Methionine | | | | | | | | | 0.005 | |
| Menthol | | | 0.05 | 0.05 | | | 0.05 | 0.05 | 0.05 | |
| Citric Acid | | | | 0.02 | 0.015 | 0.015 | | 0.002 | 0.002 | |
| Disodium Edetate | | | | | | | 0.01 | | | |
| pH | 5.09 | 4.99 | 5.11 | 4.71 | 4.01 | 4 | 4.43 | 3.9 | 3.85 | No Data | values = % w/w

Stability Data

The formulations listed in Table 1 were subject to stability test at 40° C.±2° C. under 75%±5% relative humidity for six months. Stability data was collected at zero, and six months. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Table 2 as a percentage of the area of each formulation along with amount of total impurities.

TABLE 2

Stability Data for Sublingual Buprenorphine Spray Formulations stored at 40° C. ± 2° C. under 75% ± 5% relative humidity.

| | Control | | #1 | | #2 | | #3 | | #4 | |
|---|---|---|---|---|---|---|---|---|---|---|
| Time (m) | 0 | 6 | 0 | 6 | 0 | 6 | 0 | 6 | 0 | 6 |
| Assay | 100 | 104 | 100 | 104.2 | 100 | 104.1 | 100 | 103.3 | 100 | 102.7 |
| A | BQL | ND | BQL | ND | ND | ND | BQL | ND | ND | ND |

TABLE 2-continued

Stability Data for Sublingual Buprenorphine Spray Formulations stored at 40° C. ± 2° C. under 75% ± 5% relative humidity.

| | | | | | | | | | | |
|---|---|---|---|---|---|---|---|---|---|---|
| B | ND | 0.27 | ND | 0.09 | ND | 0.06 | ND | 0.21 | ND | 0.05 |
| D | ND | BQL | ND | ND | ND | ND | ND | ND | ND | ND |
| G | BQL | 0.64 | ND | 0.06 | ND | BQL | ND | 0.11 | 0.11 | 0.68 |
| H | ND | ND | ND | ND | ND | ND | ND | ND | ND | ND |
| Bisalkyl-buprenorphine | ND | ND | ND | 0.31 | ND | BQL | ND | ND | ND | ND |
| Unspecified | BQL | ND | ND | ND | ND | ND | ND | ND | ND | ND |
| Total (% area) | 0 | 0.91 | 0 | 0.46 | 0 | 0.06 | 0 | 0.32 | 0.11 | 0.73 |

| | #5 | | #6 | | #7 | | #8 | | #9 | |
|---|---|---|---|---|---|---|---|---|---|---|
| Time (m) | 0 | 6 | 0 | 6 | 0 | 6 | 0 | 6 | 0 | 6 |
| Assay | 100 | 99.2 | 100 | 99.3 | 100 | 99.6 | 100 | 98.2 | 100 | 101.8 |
| A | ND | ND | ND | 0.06 | ND | BQL | ND | 0.05 | ND | ND |
| B | ND | 0.09 | ND | 0.17 | ND | 0.08 | ND | 0.2 | ND | BQL |
| D | ND | ND | ND | ND | ND | ND | ND | ND | ND | ND |
| G | 0.09 | 0.77 | ND | 0.07 | ND | ND | ND | 0.34 | ND | 0.4 |
| H | ND | ND | ND | 0.08 | ND | ND | ND | ND | ND | BQL |
| Bisalkyl-buprenorphine | ND | ND | ND | 0.05 | ND | ND | ND | ND | ND | ND |
| Unspecified | ND | 0.06 | BQL | ND | 0.05 | 0.08 | 0.06 | 0.21 | ND | ND |
| Total (% area) | 0.09 | 0.92 | 0 | 0.43 | 0.05 | 0.16 | 0.06 | 0.8 | 0 | 0.4 |

BQL = Below Quantifiable Limit;
ND = Not Detected

Sublingual buprenorphine spray formulations contained less than one percent total impurities after six months at 40° C. Control and formulations 1, 3, 4, 5, 6, 8 and 9 showed significant increase in levels of individual impurities (impurity B, impurity G, bisalkyl or unspecified impurity) at the 6 month time point whereas formulations containing BHA and BHT (#2) or sodium thiosulfate (#7) showed good stability. pH also played a role in the stability of the product. These results represent sublingual buprenorphine spray formulations that would remain stable for two years at room temperature.

Example 2: Stable Buprenorphine/Naloxone Formulations

Method of Making the Formulations

Sublingual spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Buprenorphine and naloxone were added to the final solution and mixed until dissolved.

Formulations

TABLE 3

Stable Buprenorphine/Naloxone Sublingual Spray Formulations

| Formulation | Control #2 | #10 | #11 | #12 | #13 |
|---|---|---|---|---|---|
| Buprenorphine HCl | 8.602 | 8.602 | 8.602 | 8.602 | 8.602 |
| Naloxone HCl | 2.44 | 2.44 | 2.44 | 2.44 | 2.44 |
| Water (USP) | 28.958 | 28.9455 | 28.943 | 28.938 | 28.933 |
| Ethanol | 55 | 55 | 55 | 55 | 55 |

TABLE 3-continued

Stable Buprenorphine/Naloxone Sublingual Spray Formulations

| Formulation | Control #2 | #10 | #11 | #12 | #13 |
|---|---|---|---|---|---|
| Propylene Glycol | 5 | 5 | 5 | 5 | 5 |
| BHA | | | | 0.01 | |
| BHT | | | | 0.005 | |
| Sodium Ascorbate | | | | | 0.02 |
| Sodium Thiosulfate | | 0.01 | 0.01 | | |
| Citric Acid | | 0.0025 | | | |
| Disodium Edetate | | | 0.005 | 0.005 | 0.005 | values = % w/w

Stability Data

The formulations listed in Table 3 were subject to stability test at 40° C.±2° C. under 75%±5% relative humidity three months and at ±25° C. under 60%±5% relative humidity for three months. Stability data was collected at zero, one, two and three months at 40° C. and at zero, one and three months at 25° C. Assay and impurities were detected using high performance liquid chromatography with an ultraviolet detector. Buprenorphine assay was performed at 288 nm and indicated as a % of initial concentration. For all buprenorphine impurities, analysis was performed at 240 nm and expressed as a % area. Naloxone assay was performed at 280 nm and indicated as a % of initial concentration and for all naloxone impurities, analysis was performed at 230 nm. Amounts of particular impurities are listed in Tables 4 and 5 for 40° C. and in Table 6 for 25° C. as a percentage of the area of each formulation along with amount of total impurities. Relative retention time ("RRT") is given for each impurity.

TABLE 4

Stability Data for Control #2 stored at 40° C. ± 2° C./75% ± 5% relative humidity for 1, 2 and 3 months.

| 40° C. Buprenorphine | RRT | 0 m | 1 m | 2 m | 3 m | 40° C. Naloxone | RRT | 0 m | 1 m | 2 m | 3 m |
|---|---|---|---|---|---|---|---|---|---|---|---|
| Assay |  | 100% | 96.93% | 94.22% | 94.27% | Assay |  | 100% | 96.31% | 97.22% | 95.62% |
| Impurity B | 0.4 | ND | ND | 0.09% | 0.12% | Impurity C | 0.66 | ND | 1.11% | 1.71% | 2.02% |
| Impurity J | 1.1 | ND | ND | BQL | BQL | Impurity A | 0.83 | ND | ND | 0.10% | 0.19% |
| Impurity F | 1.27 | ND | ND | BQL | BQL | Impurity E | 2.85 | ND | ND | 0.09% | ND |
| Impurity G | 1.8 | 0.11% | 1.84% | 3.10% | 4.14% | Impurity D | 0.20 | ND | ND | ND | 0.09% |
| Unknown | 0.26 | ND | ND | ND | BQL | Unknown | 0.28 | ND | 0.09% | 0.17% | 0.23% |
| Impurities | 0.86 | ND | 0.28% | 0.46% | 0.63% | Impurities | 0.30 | ND | ND | 0.09% | 0.17% |
|  | 2.15 | ND | 0.23% | 0.33% | 0.42% |  | 0.47 | ND | ND | ND | 0.06% |
| Total (% area) |  | 0.11% | 2.35% | 3.98% | 5.31% |  | 0.52 | ND | 0.34% | 0.73% | 1.17% |
|  |  |  |  |  |  |  | 4.30 | ND | ND | ND | 0.33% |
|  |  |  |  |  |  | Total (% area) |  | 0.00% | 1.54% | 2.89% | 4.26% |

BQL = Below Qantifiable Limit;
ND = Not Detected

The control formulation for the buprenorphine/naloxone sublingual spray formulation contained greater than 1% impurities of both buprenorphine and naloxone within one month at 40° C. and between about 4% and about 5% at three months.

TABLE 5

Stability Data for Buprenorphine/Naloxone Sublingual Spray Formulations stored at 40° C. ± 2° C./75% ± 5% relative humidity for 1, 2 and 3 months.

| 40° C. Buprenorphine | RRT | #10 | | | | RRT | #11 | | | |
|---|---|---|---|---|---|---|---|---|---|---|
|  |  | 0 m | 1 m | 2m | 3 m |  | 0 m | 1 m | 2 m | 3 m |
| Assay |  | 100% | 98.72% | 96.90% | 100.06% |  | 100% | 99.26% | 98.91% | 99.96% |
| Impurity G |  |  |  |  |  |  |  |  |  |  |
| Total (% area) |  | 0.00% | 0.00% | 0.00% | 0.00% |  | 0.00% | 0.00% | 0.00% | 0.00% |
| Naloxone | RRT | 0 m | 1 m | 2 m | 3 m | RRT | 0 m | 1 m | 2 m | 3 m |
| Assay |  | 100% | 99.19% | 102.69% | 102.42% |  | 100% | 99.84% | 102.75% | 102.00% |
| Impurity C |  |  |  |  |  |  |  |  |  |  |
| Unknown Impurities |  |  |  |  |  |  |  |  |  |  |
| Total (% area) |  | 0.00% | 0.00% | 0.00% | 0.00% |  | 0.00% | 0.00% | 0.00% | 0.00% |
| 40° C. Buprenorphine | RRT | #12 | | | | RRT | #13 | | | |
|  |  | 0 m | 1 m | 2 m | 3 m |  | 0m | 1 m | 2 m | 3 m |
| Assay |  | 100 | 99.50% | 101.44% | 101.22% |  | 100% | 99.06% | 100.30% | 99.36% |
| Impurity G | 1.8 | ND | ND | ND | 0.05% |  |  |  |  |  |
| Total (% area) |  | 0.00% | 0.00% | 0.00% | 0.05% |  | 0.00% | 0.00% | 0.00% | 0.00% |
| Naloxone | RRT | 0 m | 1 m | 2 m | 3 m | RRT | 0m | 1 m | 2 m | 3 m |
| Assay |  | 100% | 97.91% | 102.36% | 103.11% |  | 100% | 101.42% | 102.72% | 103.38% |
| Impurity C | 0.66 | ND | ND | 0.11% | 0.14% | 0.66 | ND | ND | ND | 0.09% |
| Unknown Impurities | 0.52 | ND | ND | 0.07% | 0.12% | 0.52 | ND | ND | BQL | ND |
|  | 4.02 | ND | ND | ND | ND |  |  |  |  |  |
| Total (% area) |  | 0.00% | 0.00% | 0.18% | 0.26% |  | 0.00% | 0.00% | 0.00% | 0.09% |

BQL = Below Qantifiable Limit;
ND = Not Detected

All formulations had less than 1% total impurities at three months. Similar to the buprenorphine only formulations in Example 1, formulations containing sodium thiosulfate (#10 and #11) were exceptionally stable with no impurities after three months. Formulation #12 contains BHA and BHT as the antioxidant and had significant impurities of naloxone (0.26% total impurities). Formulation #13 contains sodium ascorbate and had no impurities of buprenorphine and 0.09% total impurities of naloxone. These results represent sublingual spray formulations that would remain stable for one year at room temperature.

lations of the present invention after administration in healthy volunteers under fasting conditions.

The study was a single center, single dose, open-label, 1-sequence, 2-period, ascending dose study design in twelve healthy male and female subjects. The following dose levels of the investigational product were administered under fasting conditions: Dose 1: A single 0.5 mg dose (1 spray of 100 microliters) of Buprenorphine 5 mg/mL Sublingual Spray; and Dose 2: A single 1.0 mg dose (2 sprays of 100 microliters) of Buprenorphine 5 mg/mL Sublingual Spray.

TABLE 6

Stability Data for Buprenorphine/Naloxone Sublingual Spray Formulations stored at 25° C. ± 2° C./60% ± 5% relative humidity for 1, 2 and 3 months.

| 25° C. | | Control #2 | | | | #10 | | | | #11 | | |
|---|---|---|---|---|---|---|---|---|---|---|---|---|
| Buprenorphine | RRT | 0 m | 1 m | 3m | RRT | 0m | 1 m | 3 m | RRT | 0 m | 1 m | 3 m |
| Assay | | 100% | 97.33% | 98.25% | | 100% | 100.14% | 98.82% | | 100% | 100.01% | 99.80% |
| Impurity G | 1.8 | 0.11% | 0.44% | 1.08% | | | | | | | | |
| Unknown | 0.86 | ND | ND | 0.13% | | | | | | | | |
| Impurities | 1.8 | ND | ND | 0.09% | | | | | | | | |
| Total (% area) | | 0.11% | 0.44% | 1.30% | | 0.00% | 0.00% | 0.00% | | 0.00% | 0.00% | 0.00% |
| Naloxone | RRT | 0 m | 1 m | 3 m | RRT | 0 m | 1 m | 3 m | RRT | 0 m | 1 m | 3 m |
| Assay | | 100% | 98.56% | 100.00% | | 100% | 99.08% | 101.67% | | 100% | 99.03% | 102.16% |
| Impurity C | 0.66 | ND | 0.41% | 0.97% | | | | | | | | |
| Impurity A Unknown | 0.28 | ND | ND | 0.08% | | | | | | | | |
| Impurities | 0.52 | ND | ND | 0.13% | | | | | | | | |
| Total (% area) | | 0.00% | 0.41% | 1.18% | 0.93% | 0.00% | 0.00% | | | 0.00% | 0.00% | 0.00% |

| 25° C. | | #12 | | | | #13 | | |
|---|---|---|---|---|---|---|---|---|
| Buprenorphine | RRT | 0 m | 1 m | 3 m | RRT | 0 m | 1 m | 3 m |
| Assay | | 100 | 101.29% | 100.14% | | 100% | 98.37% | 99.74% |
| Impurity G | | | | | | | | |
| Unknown | | | | | | | | |
| Impurities | | | | | | | | |
| Total (% area) | | 0.00% | 0.00% | 0.00% | | 0.00% | 0.00% | 0.00% |
| Naloxone | RRT | 0 m | 1 m | 3 m | RRT | 0 m | 1 m | 3 m |
| Assay | | 100% | 99.03% | 101.77% | | 100% | 100.65% | 102.67% |
| Impurity C | | | | | | | | |
| Impurity A | | | | | 0.83 | ND | ND | 0.11% |
| Unknown Impurities | | | | | 0.52 | ND | ND | BQL |
| Total (% area) | | 0.00% | 0.00% | 0.00% | | 0.00% | 0.00% | 0.11% |

BQL = Below Qantifiable Limit;
ND = Not Detected

The control formulation had greater than 1% impurities at three months. All formulations containing antioxidants had less than 1% total impurities at three months. Similar to the buprenorphine only formulations in Example 1, formulations containing sodium thiosulfate (#10 and #11) or a mixture of BHA and BHT (#12) were exceptionally stable with no impurities after three months. Formulation #13 which contains sodium ascorbate had no impurities of buprenorphine and 0.11% total impurities of naloxone after storage at 25° C.±2° C./75%±5% relative humidity.

Example 3: Pharmacokinetics of Buprenorphine Sublingual Spray Formulations

A study was designed and executed to determine the pharmacokinetics of buprenorphine sublingual spray formu- The subjects arrived at the clinical site more than 10 hours before the buprenorphine administration. The subjected were supervised overnight (while fasting) and a single 50 mg dose of naltrexone (1×50 mg tablet) was orally administered with 240 mL of water approximately 1 hour prior to the buprenorphine administration to provide blockade of the pharmacological effects of buprenorphine. Then, a single dose (0.5 mg in period 1 and 1.0 mg in period 2) of the buprenorphine formulation was sublingually administered in the morning. Subjects were allowed to leave the clinical site after the 24-hour post-dose blood draw and returned to the clinical site before the remaining blood sample. The second dose level was administered following favorable safety review. The buprenorphine administrations were separated by a wash-out of 14 calendar days. The parameters are summarized below in Table 7.

TABLE 7

| Summary of Pharmacokinetic Parameters | | | | |
|---|---|---|---|---|
| | Buprenorphine 0.5 mg | | Buprenorphine 1 mg | |
| Parameter | MEAN | C.V. | MEAN | C.V. |
| $C_{max}$ (ng/mL) | 0.761 | 19.0 | 1.38 | 10.2 |
| $\ln(C_{max})$ | −0.2904 | −67.1 | 0.3169 | 31.2 |
| $T_{max}$ (hours) * | 1.75 | 30.8 | 1.50 | 30.6 |
| $AUC_{0-T}$ (ng · h/mL) | 4.37 | 13.6 | 9.12 | 10.7 |
| $\ln(AUC_{0-T})$ | 1.4671 | 9.0 | 2.2053 | 5.0 |
| $AUC_{0-\infty}$ (ng · h/mL) | 4.81 | 13.3 | 10.2 | 10.6 |
| $\ln(AUC_{0-\infty})$ | 1.5614 | 8.7 | 2.3170 | 4.7 |
| $AUC_{0-T/\infty}$ (%) | 91.19 | 6.6 | 89.49 | 3.5 |
| $\lambda_Z$ (hours$^{-1}$) | 0.0959 | 53.3 | 0.0313 | 17.0 |
| $T_{half}$ (hours) | 9.75 | 57.4 | 22.87 | 20.1 |
| $V_D$/F (L) | 1450 | 54.9 | 3250 | 19.4 |
| Cl/F (L/h) | 106 | 13.8 | 99.1 | 11.2 |
| $C_{max}$/D (ng/mL) | 0.761 | 19.0 | 0.690 | 10.2 |
| $\ln(C_{max}/D)$ | −0.2904 | −67.1 | −0.3763 | −26.3 |
| $AUC_{0-T}$/D (ng · h/mL) | 4.37 | 13.6 | 4.56 | 10.7 |
| $\ln(AUC_{0-T}/D)$ | 1.4671 | 9.0 | 1.5122 | 7.3 |
| $AUC_{0-\infty}$/D (ng · h/mL) | 4.81 | 13.3 | 5.10 | 10.6 |
| $\ln(AUC_{0-\infty}/D)$ | 1.5614 | 8.7 | 1.6238 | 6.7 |

* $T_{max}$, the median is presented

As seen in Table 7, the $C_{max}$ obtained for buprenorphine were 0.761 ng/mL and 1.38 ng/mL. The $T_{max}$ observed for buprenorphine was 1.75 and 1.50 hours following the ascending doses.

Example 4: Bioavailability of Buprenorphine

A study was designed and executed in order to compare the rate and extent of absorption and bioavailability of 1 mg buprenorphine sublingual spray formulations of the present invention with 0.3 mg (1 mL) Buprenex® (buprenorphine HCl) intramuscular injection and 0.3 mg (1 mL) Buprenex® (buprenorphine HCl) intravenous bolus injection.

This was an open-label, 3-treatment, 3-period, 6-sequence, single-dose, randomized crossover study. Eighteen healthy male and female volunteers were randomly assigned to 1 of 6 treatment sequences. Dosing occurred after an overnight fast and there was a minimum 14-day washout between the dosing in two periods. Blood samples for the measurement of the plasma concentrations of buprenorphine were collected before (pre-dose) and at 5, 10, 20, 30, and 40 minutes and at 1, 1.25, 1.5, 2, 4, 6, 8, 10, 12, 16, 24, 36, 48, 72, 96, 120, and 144 hours after dosing. The results of this study are summarized below in Table 8.

TABLE 8

| Bioavailability of Buprenorphine | | | |
|---|---|---|---|
| Parameter* | Sublingual Spray 1 mg | Intramuscular 0.3 mg | Intravenous 0.3 mg |
| Cmax (ng/mL) | 1.20 ± 0.507 (18) | 1.73 ± 1.08 (18) | 3.95 ± 3.66 (18) |
| Tmax (h) | 1.50 (18) [0.50-2.00] | 0.17 (18) [0.083-1.50] | 0.083 (18) [0.083-0.333] |
| AUC(0-t) (h × ng/mL) | 7.31 ± 2.80 (18) | 4.97 ± 1.08 (18) | 5.09 ± 1.01 (18) |
| AUC(inf) (h × ng/mL) | 8.19 ± 3.27 (15) | 5.50 ± 0.83 (15) | 5.51 ± 1.21 (17) |
| λz (1/h) | 0.0551 ± 0.0357 (15) | 0.0655 ± 0.0210 (15) | 0.1028 ± 0.0641 (17) |
| t½ (h) | 17.1 ± 8.62 (15) | 12.0 ± 5.31 (15) | 9.37 ± 6.49 (17) |

The absolute bioavailability of buprenorphine, based on AUC(0-t) and AUC(inf), after sublingual administration was 41.03% and 42.57%, respectively.

Example 5: Buprenorphine Spray Droplet Size Distribution, Spray Pattern and Plume Geometry A challenge of creating a buprenorphine sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life. Applicants found during testing that formulations of the present invention yielded desirable droplet sizes for sublingual administration. The testing also revealed that the formulation dose remains consistent when administered with a spray pump.

Five milligram per mL buprenorphine spray formulations of the present invention were subjected to two different storage conditions (25 and 40 degrees C.) and samples were taken at two different times (5M and 6M) for spray droplet size distribution analysis. Droplet analysis was conducted using standard laser analysis procedures known by those of skill in the art.

Droplet size distribution (Dv20, Dv50, Dv90, percent droplets less than 10 micrometers in diameter, D(4,3) and Span tested at two distances, 3 cm and 6 cm for upright and horizontal samples stored at 25 and 40 degrees C.) and spray pattern (Dmin, Dmax and ovality ratio tested at two distances, 3 cm and 6 cm for upright and horizontal samples stored at 25 and 40 degrees C.) were determined. D(4,3) refers to the volume moment mean of the particles; Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90-Dv10)/Dv50; DSD refers to droplet size distribution; the temperature listed is the storage temperature; U refers to an upright position of the spray pump; and H refers to horizontal position of the spray pump. The results of these studies can be seen below in Tables 9 to 40.

In addition, the formulations were tested for plume geometry including width and angle using standard procedures known by those of skill in the art. This testing showed that the spray pattern and plume were acceptable for formulations of the present invention. The results of these studies can be seen below in Tables 41 and 42.

TABLE 9

Droplet Size Distribution at 3 cm for sample stored at 25 degrees C., Upright position, 5 M

| | DSD 3 cm 25° C. - U | Dv(10) (μm) | Dv(50) (μm) | Dv(90) (μm) | % < 10μ | D(4, 3) (μm) | Span |
|---|---|---|---|---|---|---|---|
| Range | Mean | 25.37 | 53.25 | 111.1 | 0.9507 | 62.07 | 1.609 |
| | Min | 24.38 | 51.44 | 106.0 | 0.8534 | 59.51 | 1.539 |
| | Max | 26.20 | 55.85 | 119.4 | 1.0410 | 65.72 | 1.705 |

TABLE 10

Droplet Size Distribution at 6 cm for sample stored at 25 degrees C., Upright position, 5 M

| | DSD 6 cm 25° C. - U | Dv(10) (μm) | Dv(50) (μm) | Dv(90) (μm) | % < 10μ | D(4, 3) (μm) | Span |
|---|---|---|---|---|---|---|---|
| | Mean | 30.58 | 56.68 | 102.7 | 1.5794 | 62.37 | 1.270 |
| Range | Min | 28.93 | 52.00 | 90.5 | 1.4610 | 56.45 | 1.171 |
| | Max | 31.60 | 60.47 | 113.4 | 1.7840 | 57.41 | 1.355 |

TABLE 11

Droplet Size Distribution at 3 cm for sample stored at 25 degrees C., Horizontal position, 5 M

| | DSD 3 cm 25° C. - H | Dv(10) (μm) | Dv(50) (μm) | Dv(90) (μm) | % < 10μ | D(4, 3) (μm) | Span |
|---|---|---|---|---|---|---|---|
| | Mean | 24.65 | 53.78 | 138.2 | 0.7813 | 72.37 | 2.123 |
| Range | Min | 21.87 | 50.76 | 105.8 | 0.0000 | 59.42 | 1.593 |
| | Max | 26.70 | 58.10 | 194.5 | 1.1560 | 89.39 | 3.295 |

TABLE 12

Droplet Size Distribution at 6 cm for sample stored at 25 degrees C., Horizontal position, 5 M

| | DSD 6 cm 25° C. - H | Dv(10) (μm) | Dv(50) (μm) | Dv(90) (μm) | % < 10μ | D(4, 3) (μm) | Span |
|---|---|---|---|---|---|---|---|
| | Mean | 30.18 | 55.86 | 108.3 | 0.8612 | 68.69 | 1.403 |
| Range | Min | 26.86 | 52.98 | 96.1 | 0.0637 | 63.28 | 1.171 |
| | Max | 32.03 | 59.90 | 124.7 | 1.6630 | 74.75 | 1.782 |

TABLE 13

Droplet Size Distribution at 3 cm for sample stored at 40 degrees C., Upright position, 5 M

| | DSD 3 cm 40° C. - U | Dv(10) (μm) | Dv(50) (μm) | Dv(90) (μm) | % < 10μ | D(4, 3) (μm) | Span |
|---|---|---|---|---|---|---|---|
| | Mean | 26.75 | 56.64 | 120.3 | 0.9120 | 66.53 | 1.651 |
| Range | Min | 26.22 | 55.44 | 116.8 | 0.7907 | 65.09 | 1.612 |
| | Max | 27.33 | 58.02 | 122.7 | 0.9900 | 67.94 | 1.689 |

TABLE 14

Droplet Size Distribution at 6 cm for sample stored at 40 degrees C., Upright position, 5 M

| | DSD 6 cm 40° C. - U | Dv(10) (μm) | Dv(50) (μm) | Dv(90) (μm) | % < 10μ | D(4, 3) (μm) | Span |
|---|---|---|---|---|---|---|---|
| | Mean | 32.87 | 63.39 | 121.7 | 1.3128 | 71.44 | 1.390 |
| Range | Min | 31.62 | 59.93 | 111.7 | 0.6002 | 66.68 | 1.280 |
| | Max | 35.85 | 79.44 | 174.7 | 1.5100 | 94.26 | 1.748 |

TABLE 15

Droplet Size Distribution at 3 cm for sample stored at 40 degrees C., Upright position, 5 M

| | DSD 3 cm 40° C. - H | Dv(10) (μm) | Dv(50) (μm) | Dv(90) (μm) | % < 10μ | D(4, 3) (μm) | Span |
|---|---|---|---|---|---|---|---|
| | Mean | 26.08 | 55.51 | 116.1 | 0.8906 | 64.59 | 1.619 |
| Range | Min | 24.86 | 51.65 | 104.2 | 0.7230 | 59.27 | 1.530 |
| | Max | 27.12 | 58.59 | 126.6 | 1.0880 | 69.05 | 1.710 |

TABLE 16

Droplet Size Distribution at 6 cm for sample stored at 40 degrees C., Horizontal position, 5 M

| | DSD 6 cm 40° C. - H | Dv(10) (μm) | Dv(50) (μm) | Dv(90) (μm) | % < 10μ | D(4, 3) (μm) | Span |
|---|---|---|---|---|---|---|---|
| | Mean | 30.96 | 57.88 | 105.6 | 1.5678 | 63.84 | 1.288 |
| Range | Min | 29.43 | 54.51 | 97.5 | 1.1350 | 59.57 | 1.195 |
| | Max | 31.84 | 62.23 | 120.3 | 1.7230 | 70.09 | 1.429 |

TABLE 17

Plume Geometry at 3 cm for sample stored at 40 degrees C., Upright position, 5M

| | Spray Pattern 3 cm 40° C.-U | Dmin (mm) | Dmax (mm) | Ovality Ratio |
|---|---|---|---|---|
| | Mean | 12.8 | 20.0 | 1.584 |
| Range | Min | 11.6 | 17.2 | 1.289 |
| | Max | 13.6 | 24.7 | 2.043 |

TABLE 18

Plume Geometry at 6 cm for sample stored at 25 degrees C., Upright position, 5M

| | Spray Pattern 6 cm 25° C.-H | Dmin (mm) | Dmax (mm) | Ovality Ratio |
|---|---|---|---|---|
| | Mean | 21.4 | 29.1 | 1.362 |
| Range | Min | 20.2 | 27.1 | 1.228 |
| | Max | 22.5 | 32.0 | 1.511 |

TABLE 19

Plume Geometry at 3 cm for sample stored at 25 degrees C., Upright position, 5M

| | Spray Pattern 3 cm 25° C.-H | Dmin (mm) | Dmax (mm) | Ovality Ratio |
|---|---|---|---|---|
| Range | Mean | 13.6 | 19.5 | 1.436 |
| | Min | 13.0 | 18.0 | 1.382 |
| | Max | 14.2 | 21.1 | 1.580 |

TABLE 20

Plume Geometry at 6 cm for sample stored at 25 degrees C., Upright position, 5M

| | Spray Pattern 6 cm 25° C.-U | Dmin (mm) | Dmax (mm) | Ovality Ratio |
|---|---|---|---|---|
| Range | Mean | 21.3 | 30.1 | 1.421 |
| | Min | 19.9 | 26.7 | 1.244 |
| | Max | 22.3 | 33.4 | 1.679 |

TABLE 21

Plume Geometry at 3 cm for sample stored at 25 degrees C., Upright position, 5M

| | Spray Pattern 3 cm 25° C.-U | Dmin (mm) | Dmax (mm) | Ovality Ratio |
|---|---|---|---|---|
| Range | Mean | 14.4 | 19.1 | 1.320 |
| | Min | 13.2 | 17.1 | 1.212 |
| | Max | 15.9 | 22.3 | 1.426 |

TABLE 22

Plume Geometry at 3 cm for sample stored at 40 degrees C., Horizontal position, 5M

| | Spray Pattern 3 cm 40° C.-H | Dmin (mm) | Dmax (mm) | Ovality Ratio |
|---|---|---|---|---|
| Range | Mean | 13.0 | 18.3 | 1.415 |
| | Min | 12.3 | 16.1 | 1.180 |
| | Max | 13.9 | 21.3 | 1.662 |

TABLE 23

Plume Geometry at 6 cm for sample stored at 40 degrees C., Upright position, 5M

| | Spray Pattern 6 cm 40° C.-U | Dmin (mm) | Dmax (mm) | Ovality Ratio |
|---|---|---|---|---|
| Range | Mean | 20.8 | 32.2 | 1.578 |
| | Min | 18.3 | 25.3 | 1.151 |
| | Max | 22.2 | 43.2 | 2.317 |

TABLE 24

Plume Geometry at 6 cm for sample stored at 40 degrees C., Horizontal position, 5M

| | Spray Pattern 6 cm 40° C.-H | Dmin (mm) | Dmax (mm) | Ovality Ratio |
|---|---|---|---|---|
| Range | Mean | 21.5 | 29.4 | 1.371 |
| | Min | 19.8 | 27.1 | 1.253 |
| | Max | 23.3 | 32.5 | 1.639 |

TABLE 25

Droplet Size Distribution at 3 cm for sample stored at 25 degrees C., Upright position, 6 M

| | DSD 3 cm 25° C. - U | Dv(10) (μm) | Dv(50) (μm) | Dv(90) (μm) | % < 10μ | D(4, 3) (μm) | Span |
|---|---|---|---|---|---|---|---|
| Range | Mean | 26.22 | 57.53 | 121.8 | 0.5523 | 67.25 | 1.652 |
| | Min | 24.63 | 50.98 | 104.4 | 0.0000 | 59.18 | 1.544 |
| | Max | 27.73 | 68.01 | 148.6 | 0.9883 | 79.42 | 1.783 |

TABLE 26

Droplet Size Distribution at 6 cm for sample stored at 25 degrees C., Upright position, 6 M

| | DSD 6 cm 25° C. - U | Dv(10) (μm) | Dv(50) (μm) | Dv(90) (μm) | % < 10μ | D(4, 3) (μm) | Span |
|---|---|---|---|---|---|---|---|
| Range | Mean | 31.87 | 62.59 | 119.9 | 1.1915 | 70.21 | 1.405 |
| | Min | 29.24 | 58.74 | 111.6 | 0.8993 | 65.79 | 1.282 |
| | Max | 33.93 | 66.29 | 133.7 | 1.4090 | 75.92 | 1.528 |

TABLE 27

Droplet Size Distribution at 3 cm for sample stored at 25 degrees C., Horizontal position, 6 M

| | DSD 3 cm 25° C. - H | Dv(10) (μm) | Dv(50) (μm) | Dv(90) (μm) | % < 10μ | D(4, 3) (μm) | Span |
|---|---|---|---|---|---|---|---|
| Range | Mean | 24.55 | 50.03 | 101.6 | 0.8918 | 57.62 | 1.538 |
| | Min | 22.88 | 46.53 | 91.7 | 0.0000 | 52.75 | 1.476 |
| | Max | 25.64 | 52.39 | 109.5 | 1.3350 | 61.24 | 1.633 |

TABLE 28

Droplet Size Distribution at 6 cm for sample stored at 25 degrees C., Horizontal position, 6 M

| | DSD 6 cm 25° C. - H | Dv(10) (μm) | Dv(50) (μm) | Dv(90) (μm) | % < 10μ | D(4, 3) (μm) | Span |
|---|---|---|---|---|---|---|---|
| Range | Mean | 29.58 | 56.85 | 105.2 | 1.3818 | 62.82 | 1.323 |
| | Min | 28.53 | 51.57 | 89.4 | 1.0870 | 55.73 | 1.178 |
| | Max | 30.75 | 60.69 | 116.4 | 1.6780 | 67.86 | 1.434 |

TABLE 29

Droplet Size Distribution at 3 cm for sample stored at 40 degrees C., Upright position, 6 M

| | DSD 3 cm 40° C. - U | Dv(10) (μm) | Dv(50) (μm) | Dv(90) (μm) | % < 10μ | D(4, 3) (μm) | Span |
|---|---|---|---|---|---|---|---|
| Range | Mean | 27.60 | 58.79 | 125.9 | 0.4862 | 69.31 | 1.669 |
| | Min | 26.50 | 52.85 | 111.3 | 0.0000 | 62.36 | 1.579 |
| | Max | 29.11 | 65.51 | 140.0 | 0.7686 | 76.44 | 1.729 |

TABLE 30

Droplet Size Distribution at 6 cm for sample stored at 40 degrees C., Upright position, 6 M

| | DSD 6 cm 40° C. - U | Dv(10) (μm) | Dv(50) (μm) | Dv(90) (μm) | % < 10μ | D(4, 3) (μm) | Span |
|---|---|---|---|---|---|---|---|
| Range | Mean | 33.68 | 67.20 | 131.3 | 1.0200 | 76.03 | 1.450 |
| | Min | 32.54 | 63.80 | 118.0 | 0.8835 | 70.69 | 1.314 |
| | Max | 35.01 | 70.75 | 141.2 | 1.4480 | 80.26 | 1.543 |

TABLE 31

Droplet Size Distribution at 3 cm for sample stored at 40 degrees C., Horizontal position, 6 M

| | DSD 3 cm 40° C. - H | Dv(10) (μm) | Dv(50) (μm) | Dv(90) (μm) | % < 10μ | D(4, 3) (μm) | Span |
|---|---|---|---|---|---|---|---|
| Range | Mean | 27.75 | 55.42 | 114.3 | 0.0005 | 64.60 | 1.559 |
| | Min | 26.47 | 52.01 | 104.6 | 0.0000 | 60.13 | 1.475 |
| | Max | 29.22 | 59.01 | 124.9 | 0.0019 | 69.62 | 1.621 |

TABLE 32

Droplet Size Distribution at 6 cm for sample stored at 40 degrees C., Horizontal position, 6 M

| | DSD 6 cm 40° C. - H | Dv(10) (μm) | Dv(50) (μm) | Dv(90) (μm) | % < 10μ | D(4, 3) (μm) | Span |
|---|---|---|---|---|---|---|---|
| Range | Mean | 34.33 | 63.86 | 118.0 | 0.9685 | 70.95 | 1.309 |
| | Min | 32.47 | 60.19 | 110.1 | 0.0624 | 66.54 | 1.251 |
| | Max | 37.21 | 68.17 | 129.6 | 1.5090 | 76.88 | 1.363 |

TABLE 33

Plume Geometry at 3 cm for sample stored at 25 degrees C., Upright position, 6M

| | Spray Pattern 3 cm 25° C.-U | Dmin (mm) | Dmax (mm) | Ovality Ratio |
|---|---|---|---|---|
| Range | Mean | 14.0 | 20.8 | 1.489 |
| | Min | 13.4 | 17.9 | 1.300 |
| | Max | 14.5 | 23.1 | 1.664 |

TABLE 34

Plume Geometry at 6 cm for sample stored at 25 degrees C., Upright position, 6M

| | Spray Pattern 6 cm 25° C.-U | Dmin (mm) | Dmax (mm) | Ovality Ratio |
|---|---|---|---|---|
| Range | Mean | 20.3 | 30.3 | 1.497 |
| | Min | 19.1 | 27.4 | 1.320 |
| | Max | 21.1 | 33.6 | 1.705 |

TABLE 35

Plume Geometry at 3 cm for sample stored at 25 degrees C., Horizontal position, 6M

| | Spray Pattern 3 cm 25° C.-H | Dmin (mm) | Dmax (mm) | Ovality Ratio |
|---|---|---|---|---|
| Range | Mean | 14.0 | 21.4 | 1.549 |
| | Min | 12.9 | 19.8 | 1.276 |
| | Max | 15.7 | 23.9 | 1.852 |

TABLE 36

Plume Geometry at 6 cm for sample stored at 25 degrees C., Horizontal position, 6M

| | Spray Pattern 6 cm 25° C.-H | Dmin (mm) | Dmax (mm) | Ovality Ratio |
|---|---|---|---|---|
| Range | Mean | 20.2 | 32.3 | 1.599 |
| | Min | 18.8 | 28.4 | 1.390 |
| | Max | 21.3 | 37.7 | 1.808 |

TABLE 37

Plume Geometry at 3 cm for sample stored at 40 degrees C., Upright position, 6M

| | Spray Pattern 3 cm 40° C.-U | Dmin (mm) | Dmax (mm) | Ovality Ratio |
|---|---|---|---|---|
| Range | Mean | 14.9 | 19.2 | 1.284 |
| | Min | 13.8 | 17.3 | 1.155 |
| | Max | 15.5 | 20.8 | 1.399 |

TABLE 38

Plume Geometry at 6 cm for sample stored at 40 degrees C., Upright position, 6M

| | Spray Pattern 6 cm 40° C.-U | Dmin (mm) | Dmax (mm) | Ovality Ratio |
|---|---|---|---|---|
| Range | Mean | 21.3 | 27.5 | 1.296 |
| | Min | 19.8 | 26.5 | 1.194 |
| | Max | 22.8 | 29.3 | 1.427 |

TABLE 39

Plume Geometry at 3 cm for sample stored at 40 degrees C., Horizontal position, 6M

| | Spray Pattern 3 cm 40° C.-H | Dmin (mm) | Dmax (mm) | Ovality Ratio |
|---|---|---|---|---|
| Range | Mean | 14.6 | 22.5 | 1.547 |
| | Min | 13.9 | 20.8 | 1.430 |
| | Max | 16.0 | 24.8 | 1.781 |

TABLE 40

Plume Geometry at 6 cm for sample stored at 40 degrees C., Horizontal position, 6M

| | Spray Pattern 6 cm 40° C.-H | Dmin (mm) | Dmax (mm) | Ovality Ratio |
|---|---|---|---|---|
| Range | Mean | 21.5 | 29.4 | 1.371 |
| | Min | 19.8 | 27.1 | 1.253 |
| | Max | 23.3 | 32.5 | 1.639 |

TABLE 41

Plume Geometry at 3 cm (width and angle)

|  | 3 cm | Width (mm) | Angle (°) |
|---|---|---|---|
| Range | Mean | 27.9 | 49.9 |
|  | Min | 25.5 | 46.1 |
|  | Max | 30.8 | 54.3 |

TABLE 42

Plume Geometry at 6 cm (width and angle)

|  | 6 cm | Width (mm) | Angle (°) |
|---|---|---|---|
| Range | Mean | 40.2 | 37.0 |
|  | Min | 36.0 | 33.4 |
|  | Max | 43.9 | 40.2 |

Example 6: Further Buprenorphine Formulations

TABLE 43

Further Buprenorphine Formulations

| Formulation | #14 | #15 | #16 | #17 | #18 |
|---|---|---|---|---|---|
| Buprenorphine HCl | 0.0813 | 0.1625 | 0.325 | 0.65 | 1.3 |
| BHA | 0.01 | 0.01 | 0.01 | 0.01 | 0.01 |
| BHT | 0.005 | 0.005 | 0.005 | 0.005 | 0.005 |
| L-Menthol | 0.05 | 0.05 | 0.05 | 0.05 | 0.05 |
| Ethanol | 55 | 55 | 55 | 55 | 55 |
| Propylene Glycol | 5 | 5 | 5 | 5 | 5 |
| Purified Water | 39.8537 | 39.7725 | 39.61 | 39.285 | 38.635 |
| Citric Acid Anhydrous | QS to pH | QS to pH | QS to pH | QS to pH | QS to pH |
| Sodium Hydroxide | QS to pH | QS to pH | QS to pH | QS to pH | QS to pH |
| Nitrogen | Sparging/Overlay | Sparging/Overlay | Sparging/Overlay | Sparging/Overlay | Sparging/Overlay |

Buprenorphine formulations of Table 43 were all stable upon preparation.

Example 7: Further Buprenorphine/Naloxone Formulations

TABLE 44

Further Buprenorphine/Naloxone Formulations

| Formulation | #19 | #20 | #21 | #22 |
|---|---|---|---|---|
| Buprenorphine HCl | 8.39 | 5.554 | 2.84 | 1.42 |
| Naloxone | 2.37 | 1.57 | 0.804 | 0.402 |
| L-Menthol | 0.05 | 0.05 | 0.05 | 0.05 |
| Edetate Disodium Dihydrate | 0.005 | 0.005 | 0.005 | 0.005 |
| Sodium Ascorbate | 0.02 | 0.02 | 0.02 | 0.02 |
| Ethanol | 55 | 55 | 55 | 55 |
| Propylene Glycol | 5 | 5 | 5 | 5 |
| Water | 29.165 | 32.801 | 36.281 | 38.103 |

Buprenorphine/naloxone formulations of Table 44 were all stable upon preparation.

What is claimed is:

1. A sublingual spray formulation comprising from 0.1625% to 1.3% w/w of buprenorphine, a pharmaceutically acceptable salt thereof, or a derivative thereof, water as a solvent, mixture of an alcohol and a glycol as a cosolvent, and from 0.005% to 0.02% w/w of an antioxidant selected from the group consisting of butylated hydroxyanisole (BHA), butylated hydroxytoluene (BHT), sodium ascorbate, sodium thiosulfate, and a mixture thereof, wherein the ratio of antioxidant to buprenorphine is from 0.004:1 to 0.1:1 and the % w/w is of the total formulation.

2. The sublingual spray formulation of claim 1 further comprising naloxone, a pharmaceutically acceptable salt thereof, or a derivative thereof.

3. A sublingual spray formulation comprising:
   buprenorphine, a pharmaceutically acceptable salt thereof or a derivative thereof in an amount from 0.1625% to 1.3% w/w;
   water as a solvent in an amount from about 10% to about 95% w/w;
   a cosolvent consisting of a mixture of about 55% w/w of an alcohol and about 5% w/w of a glycol; and
   an antioxidant selected from the group consisting of butylated hydroxyanisole (BHA), butylated hydroxytoluene (BHT), sodium ascorbate, sodium thiosulfate, and a mixture thereof, in an amount from 0.005% to 0.02% w/w,
   wherein the ratio of antioxidant to buprenorphine is from 0.004:1 to 0.1:1 and the % w/w is of the total formulation.

4. The formulation of claim 3 further comprising menthol.

5. The formulation of claim 4, wherein:
   water as a solvent is at an amount from about 38% to about 40% w/w;
   the cosolvent consists of a mixture of ethanol in an amount of 55% w/w and propylene glycol in an amount of about 5% w/w;
   the antioxidant consists of a mixture of butylated hydroxyanisole (BHA) in an amount of about 0.01% w/w and butylated hydroxytoluene (BHT) in an amount of 0.005% w/w; and
   menthol is at an amount of about 0.05% w/w,
   wherein the ratio of antioxidant to buprenorphine is from 0.01:1 to 0.1:1.

6. A sublingual spray formulation comprising:
   buprenorphine, a pharmaceutically acceptable salt thereof or a derivative thereof at an amount from 1.4% to 8.6% w/w;
   naloxone, a pharmaceutically acceptable salt thereof or a derivative thereof at an amount from about 0.005% to about 3% w/w;
   water as a solvent at an amount from about 10% w/w to 95% w/w;
   a cosolvent consisting of a mixture of about 55% of an alcohol and about 5% of a glycol;
   an antioxidant selected from the group consisting of butylated hydroxyanisole (BHA), butylated hydroxytoluene (BHT), sodium ascorbate, sodium thiosulfate, and a mixture thereof, in an amount from 0.005% to 0.02% w/w; and
   a chelating agent in an amount from about 0.001% to about 0.1% w/w,
   wherein the ratio of antioxidant to buprenorphine is from 0.0006:1 to 0.014:1 and the % w/w is of the total formulation.

7. The formulation of claim 6 further comprising menthol.

8. The sublingual spray formulation of claim 7, wherein:
   naloxone, a pharmaceutically acceptable salt thereof or a derivative thereof is at an amount from about 0.4% to about 2.4% w/w;

water as a solvent is at an amount from about 28% to about 38% w/w;
the cosolvent consists of a mixture of ethanol in an amount of 55% w/w and propylene glycol in an amount of about 5% w/w;
the antioxidant is sodium ascorbate at an amount of about 0.02% w/w;
the chelating agent is disodium edetate at an amount of about 0.005% w/w; and
menthol is at an amount of about 0.05% w/w.

9. The sublingual spray formulation of claim 1 that is capable of producing a droplet size distribution wherein greater than 98% of the composition particles are greater than 10 microns in diameter during administration.

10. The sublingual spray formulation of claim 1 that is capable of producing a droplet size distribution wherein:
the mean Dv(10) is from about 10 to about 30 microns during administration;
the mean Dv(50) is from about 30 to about 80 microns during administration; and
the mean Dv(90) is from about 80 to about 200 microns during administration.

11. The sublingual spray formulation of claim 1 that is capable of producing a spray span ((Dv90-Dv10)/Dv50) of from about 1.2 to about 3.3.

12. The sublingual spray formulation of claim 1 that is capable of producing a spray plume that has an ovality ratio of from about 1.1 to 2.4.

13. The sublingual spray formulation of claim 1 that is capable of producing a spray plume width that is from about 25 to about 45 millimeters during administration and a spray plume angle that is from about 30 to about 55 degrees during administration.

14. The sublingual spray formulation of claim 1 that is capable of producing a D(4,3) of 55 to 95 microns.

15. The sublingual spray formulation of claim 1 that is capable of producing a droplet size distribution wherein the $C_{max}$ (ng/mL) of buprenorphine is from about 0.6 to about 0.8 following administration.

16. The sublingual spray formulation of claim 1 that is capable of producing a droplet size distribution wherein the $T_{max}$ of buprenorphine is from about 1.5 to about 1.9 hours following administration.

17. A method of treating pain comprising administering the sublingual spray formulation of claim 1 to a patient in need thereof.

18. A method of treating opioid dependence comprising administering the sublingual spray formulation of claim 6 to a patient in need thereof.

* * * * *